United States Patent
Penagondla et al.

(10) Patent No.: US 12,111,309 B2
(45) Date of Patent: Oct. 8, 2024

(54) POINT OF CARE DEVICES AND METHODS FOR DETECTING INFECTION STATUS OF A WOUND

(71) Applicant: ConvaTec Limited, Flintshire (GB)

(72) Inventors: Manjunath L. Penagondla, Warrington (GB); Daniel G. Metcalf, Greater Manchester (GB); Philip G. Bowler, Warrington (GB)

(73) Assignee: CONVATEC LIMITED, Flintshire (GB)

( * ) Notice: Subject to any disclaimer, the term of this patent is extended or adjusted under 35 U.S.C. 154(b) by 181 days.

(21) Appl. No.: 17/128,938

(22) Filed: Dec. 21, 2020

(65) Prior Publication Data

US 2021/0190767 A1    Jun. 24, 2021

Related U.S. Application Data

(63) Continuation of application No. PCT/GB2020/053316, filed on Dec. 21, 2020.

(60) Provisional application No. 62/952,833, filed on Dec. 23, 2019.

(51) Int. Cl.
  *G01N 33/52*   (2006.01)
  *G01N 1/02*    (2006.01)
  *G01N 27/327*  (2006.01)

(52) U.S. Cl.
  CPC .......... *G01N 33/525* (2013.01); *G01N 1/02* (2013.01); *G01N 27/3275* (2013.01); *G01N 2001/028* (2013.01)

(58) Field of Classification Search
  None
  See application file for complete search history.

(56) References Cited

U.S. PATENT DOCUMENTS

| | | | |
|---|---|---|---|
| 5,078,968 A | 1/1992 | Nason | |
| 6,248,294 B1 * | 6/2001 | Nason | G01N 1/02 422/430 |
| 6,372,511 B1 * | 4/2002 | Silver | G01N 21/76 250/361 C |
| 11,026,847 B2 | 6/2021 | Piotrowski et al. | |
| 11,083,629 B2 | 8/2021 | Locke et al. | |
| 11,096,830 B2 | 8/2021 | Pratt et al. | |
| 11,246,758 B2 | 2/2022 | Hardman et al. | |
| 11,273,078 B2 | 3/2022 | Simmons | |
| 11,291,587 B2 | 4/2022 | Kilpadi | |

(Continued)

FOREIGN PATENT DOCUMENTS

| | | |
|---|---|---|
| EP | 2323712 B2 | 8/2021 |
| EP | 3458004 B1 | 10/2021 |

(Continued)

OTHER PUBLICATIONS

Canadian Office Action, Canadian Intellectual Property Office, Canadian Patent Application No. 3,165,269, Feb. 15, 2024, 10 pages.

*Primary Examiner* — Lore R Jarrett
(74) *Attorney, Agent, or Firm* — TAFT STETTINIUS & HOLLISTER LLP; Ryan O. White; Derek B. Lavender

(57) ABSTRACT

Wound sampling devices for detecting infection status may be used for point-of-care devices that can be placed at a wound site and detect an infection marker, infection status, or wound healing status by displaying a visible signal such as a color change.

25 Claims, 9 Drawing Sheets

(56) References Cited

U.S. PATENT DOCUMENTS

| | | |
|---|---|---|
| 11,400,204 B2 | 8/2022 | Coulthard et al. |
| 11,504,033 B2 | 11/2022 | Hicks et al. |
| 11,723,808 B2 | 8/2023 | Burnet et al. |
| 11,730,457 B2 | 8/2023 | Locke et al. |
| 2003/0143752 A1* | 7/2003 | Feldsine ............ G01N 21/8507 436/164 |
| 2005/0084842 A1 | 4/2005 | O'Connor |
| 2007/0244368 A1 | 10/2007 | Bayloff et al. |
| 2008/0206740 A1* | 8/2008 | Skiffington ............ G01N 1/02 435/5 |
| 2009/0012425 A1 | 1/2009 | Dodge et al. |
| 2009/0299161 A1 | 12/2009 | Cullen et al. |
| 2012/0258483 A1* | 10/2012 | Gubitz ............... G01N 33/6893 435/23 |
| 2014/0004548 A1* | 1/2014 | Gordon ................ G01N 21/763 422/549 |
| 2019/0151335 A1 | 5/2019 | Altschul et al. |
| 2021/0275693 A1 | 9/2021 | Ballamy |
| 2021/0290207 A1 | 9/2021 | Locke et al. |
| 2021/0338488 A1 | 11/2021 | Pratt et al. |
| 2021/0378565 A1 | 12/2021 | Kettel et al. |
| 2021/0379241 A1 | 12/2021 | Kettel et al. |
| 2022/0031520 A1 | 2/2022 | Kilpadi |
| 2022/0079509 A1 | 3/2022 | Gellman et al. |
| 2022/0151834 A1 | 5/2022 | Simmons |
| 2022/0265477 A1 | 8/2022 | Locke et al. |
| 2022/0265478 A1 | 8/2022 | Locke et al. |
| 2022/0296770 A1 | 9/2022 | Cavanaugh et al. |
| 2022/0362060 A1 | 11/2022 | Rehbein et al. |

FOREIGN PATENT DOCUMENTS

| | | |
|---|---|---|
| EP | 2544640 B1 | 11/2021 |
| EP | 3717626 B1 | 12/2021 |
| EP | 3936095 A1 | 1/2022 |
| EP | 3960137 A1 | 3/2022 |
| EP | 3421020 B1 | 5/2022 |
| EP | 2623137 B2 | 6/2022 |
| EP | 4003254 A1 | 6/2022 |
| EP | 4007551 A1 | 6/2022 |
| EP | 4007552 A1 | 6/2022 |
| EP | 4009929 A1 | 6/2022 |
| EP | 4025164 A1 | 7/2022 |
| EP | 4026525 A1 | 7/2022 |
| EP | 3582731 B1 | 8/2022 |
| EP | 4041161 A1 | 8/2022 |
| EP | 3225261 B1 | 12/2022 |
| EP | 3436012 B1 | 9/2023 |
| EP | 4007551 B1 | 9/2023 |
| EP | 3402450 B1 | 10/2023 |
| EP | 4279095 A2 | 11/2023 |
| EP | 3578209 B1 | 12/2023 |

* cited by examiner

POINT OF CARE DEVICES AND METHODS FOR DETECTING INFECTION STATUS OF A WOUND

CROSS-REFERENCE TO RELATED APPLICATIONS

This application is a continuation of International Application No. PCT/GB2020/053316 filed Dec. 21, 2020 and claims the benefit of U.S. Provisional Application No. 62/952,833 filed on Dec. 23, 2019, the contents of which are incorporated herein by reference in their entirety.

BACKGROUND

Wound healing is a complex and dynamic process. Microbial or pathogen infection is detrimental to the wound healing process, and therefore it is important to detect wound infection status as soon as possible.

At present, when a Health Care Professional (HCP) suspects that a wound may be infected, he or she will swab a wound area suspected of being infected to collect a sample of wound fluids for microbiological analysis. The HCP may suspect an infection of a wound if, for example, there is increased redness around the wound, wound exudate/pus, presence of malodour, increased swelling, tenderness, pain and/or temperature/fever occurs around the wound. However, in most chronic, non-healing wounds, such signs of infection are often masked, and are less evident to a HCP.

A sample of the exudate typically would be taken from across the wound using a sterile swab. After the sample is collected with the swab (i.e., absorbed into the swab), the swab is typically placed into a sterile vial containing a medium that will maintain viability of microorganisms during transportation to the laboratory. A typical process for taking such a sample would be to investigate the wound site, break open the sterile package containing the swab, swab the wound site, then return the swab to the vile ensuring the swab sampling area is immersed into the maintenance medium. The sample vial then would be sent to a laboratory where the contents of the swab would be cultured on a variety of microbiological culture media for the presence of micro-organisms (predominantly bacteria and yeasts). Microbiological analysis would subsequently involve identifying potentially pathogenic micro-organisms, and performing antibiotic susceptibility testing if deemed appropriate. The laboratory tester attempts to grow a sample and, if a positive result is obtained, to test the sample against various antibiotics. The results would then be reported back to the HCP and appropriate treatment would be prescribed by the HCP.

The process of microbiological analysis of a wound swab in the laboratory is complex, costly and time-consuming (commonly 2-5 days). In addition, such test results are not consistently reliable. For example, a test result from the laboratory showing the presence a potential pathogen (e.g. *Staphylococcus aureus, Pseudomonas aeruginosa*) does not necessarily mean the wound is actually infected. This may result in the HCP prescribing antibiotics based purely on the presence of potential pathogens, without these organisms actually causing an infection. Thus, incidences of false positive results are problematic Current practices for determining wound infection status (i.e. microbiological result and clinical signs of infection) are therefore prone to error, which might lead to inappropriate treatment (e.g. antibiotic therapy where it is not needed). There remains a need for solutions to the above problems, to assist the HCP in determining early wound infection status. More particularly, there is a need for a device that enables a HCP to carry out analysis of potential wound infections quickly and at the point of care (rather than sample being sent to a laboratory and tested). The proposed solution allows for the HCP to obtain a test result within minutes and at the point of care, which more accurately indicates wound infection status.

SUMMARY

The present disclosure provides devices and methods for rapid, point-of-care detection of infection status of a wound. In one aspect of the disclosure, there is provided a device for detecting an infection in a wound that includes: (a) an indicator unit; wherein the indicator unit comprises: (i) a sensor tube having an open proximal end; and (ii) a sensor positioned in the sensor tube; and (b) a swab unit, wherein the swab unit comprises: (i) a swab shaft having a proximal end and a distal end; (ii) a swab tip positioned at the distal end of the swab shaft; and (iii) a swab handle connected to the swab shaft at the proximal end of the swab shaft, the swab handle being configured to sealingly engage the open proximal end of the sensor tube. In certain embodiments, the sensor includes a carrier material and at least one substrate that is operable to undergo a visible color change in response to expression of a specific infection marker present in wound fluid. In some embodiments, the sensor includes at least two substrates, each substrate operable to undergo a visible color change in response to expression of a different marker present in wound fluid. The carrier material can include, for example, paper, cellulose, cellulose derivatives, viscose, polyamide, polyester, polyacrylate, fabric, sodium carboxymethylcellulose fiber, or cardboard. The swab tip can include, for example, cellulose, modified cellulose, polyurethane foam, polyester, silk, wool, nylon, polypropylene, elastane, or mixtures thereof.

In some embodiments, the indicator unit further comprises a sensor retaining insert sealingly engaged to a distal end of the sensor tube, and the sensor is affixed to the sensor retaining insert. In some embodiments, the sensor retaining insert defines a cavity configured to receive the swab tip when the swab unit is sealingly engaged to the indicator unit. In some embodiments, the sensor retaining insert includes at least one structural feature in or adjacent to the cavity to guide the swab tip as it enters the sensor retaining insert into a desired juxtaposition with the sensor. The at least one structural feature can be, for example, one or more rib features, inclined cavity walls and combinations thereof.

In certain embodiments, the sensor comprises a member selected from the group consisting of an enzyme-reactive indicator, a reagent that is a source of peroxide, an enzyme that is able to transform color reactions, a pH indicator, a total protein-detecting reagent, a moisture-detecting reagent and combinations thereof. An example of a pH indicator that can be employed is a pH-sensitive reagent. In some embodiments that include an enzyme-reactive indicator, the enzyme-reactive indicator comprises a moiety capable of producing a visible color or detectable electronic change upon interaction with one or more target enzymes. The moiety can be, for example, a peroxidase substrate, arylamine, an amino phenol, an indoxyl, a neutral dye, a charged dye, a nanoparticle, a colloidal gold particle, and combinations or analogs thereof.

In some embodiments, the swab handle defines a liquid chamber and the swab handle is operable to contain a liquid in the liquid chamber and release the liquid into the sensor tube after the swab tip is positioned within the sensor tube. In some embodiments, the liquid chamber contains a liquid in an amount of about 500 uL, 1 mL, 1.5 mL, 2 mL, 2.5 mL, 3 mL, 3.5 mL, or 4 mL.

In some embodiments that include a liquid chamber, the swab handle is configured for manual release of the liquid from the liquid chamber. In some embodiments, the swab handle includes a retaining element configured to attach to the sensor tube, the retaining element defining a cavity, and a movable element retained within the cavity and movable relative to the retaining element. In some embodiments, the liquid chamber is contained within the movable element. In some embodiments, the movable element further includes a liquid chamber seal, the handle further includes a piercing member fixedly attached to the retaining element, and moving the movable element from a proximal position to a distal position causes the piercing member to pierce the liquid chamber seal to release the liquid into the sensor tube. The seal can be, for example, a metallic foil or a plastic film. In some embodiments, the swab shaft is fixedly attached to the retaining element such that a proximal end of the swab shaft extends into the cavity, and the piercing member comprises the proximal end of the swab shaft. In certain embodiments, the swab shaft comprises a tube defining a longitudinal passageway therethrough, and, after the liquid chamber seal is pierced, the liquid chamber is in fluid communication with the sensor tube through the passageway. In still other embodiments, the swab shaft defines a radial aperture at its distal end near the swab tip, and, after the liquid chamber seal is pierced, the liquid chamber is in fluid communication with the sensor tube through the passageway and the aperture. In some embodiments, the swab handle further comprises a locking mechanism that is operable to prevent the movable element from moving in a proximal direction after the liquid chamber seal is pierced.

In other embodiments that include a liquid chamber, the swab handle is configured for automatic release of the liquid from the liquid chamber when the handle of the swab unit is sealingly engaged to the open proximal end of the sensor tube. In some embodiments, the swab handle comprises a liquid chamber seal positioned at a distal end of the liquid chamber, the indicator unit further comprises a piercing member fixedly attached to the sensor tube at a location whereby the piercing member contacts the liquid chamber seal only when the distal end is inserted into the sensor tube, and inserting the distal end into the sensor tube causes the piercing member to pierce the liquid chamber seal to release the liquid into the sensor tube. In some embodiments, the piercing member is a piercing ring.

In another aspect, the present disclosure provides a method for detecting a marker in a wound that includes: (a) contacting the wound with the swab tip of any detecting device disclosed herein; (b) inserting the swab tip inside the sensor tube and sealingly engaging the swab unit to the indicator unit; and (c) observing a change in the sensor. In some embodiments, the change is a color change, a fluorescent signal, a luminescent signal, or an electrical change. In some embodiments, the sensor includes a carrier material and at least one substrate that is operable to undergo a visible change color change in response to expression of a specific infection marker present in wound fluid released from the swab tip. In some embodiments, the method further includes (d) comparing the signal to a reference or a control to determine a level of the infection marker. In some embodiments in which the device includes a movable element, the method further includes pressing the movable element following step (b). In some embodiments, step (b) comprises placing the swab tip of the swab unit in contact with the sensor of the indicator unit. In some embodiments, step (b) results in piercing of a liquid seal. In some embodiments, the piercing of the liquid seal releases liquid into the sensor tube.

Further features, characteristics, and embodiments of the present disclosure will be apparent from the detailed description herein.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION

Definitions

Figure 1:
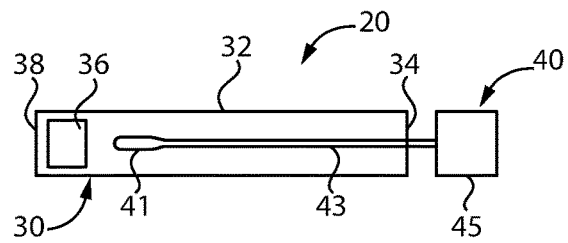
FIG. 1 illustrates a schematic view of one wound sampling device embodiment comprising a swab unit and an indicator unit.

As used herein the term "wound" refers to an injury to living tissue as may be caused, for example, by a cut, blow, or other impact, typically one in which the skin is cut, broken or otherwise damaged. Examples of wounds include, but are not limited to, abdominal wounds or other large or incisional wounds (either as a result of surgery, trauma, stemiotomies, fasciotomies, or other conditions), dehisced wounds, acute wounds, chronic wounds, subacute and dehisced wounds, traumatic wounds (such as from orthopaedic trauma), flaps and skin grafts, lacerations, abrasions, contusions, burns, diabetic ulcers, pressure ulcers, stoma, surgical wounds, trauma and venous ulcers, broken bones or the like. Wounds may also include a deep tissue injury, Deep tissue injury is a term proposed by the National Pressure Ulcer Advisory Panel (NPUAP) to describe a unique form of pressure ulcers. These ulcers have been described by clinicians for many years with terms such as purple pressure ulcers, ulcers that are likely to deteriorate and bruises on bony prominences.

A wound may be a chronic or acute injury. The technology disclosed can be used on an acute or chronic wound. Acute wounds typically occur as a result of surgery or trauma and typically move through certain known stages of healing within a predicted timeframe. Chronic wounds often begin as acute wounds, and an acute wound can become a chronic wound when it does not follow the healing stages of acute wounds, which results in a lengthened recovery. It is believed that the transition from acute to chronic wound can, in some instances, result from a patient being immunocompromised. Chronic wounds may include for example: venous ulcers (such as those that occur in the legs), which account for the majority of chronic wounds and mostly affect the elderly: diabetic ulcers (for example, foot or ankle ulcers); peripheral arterial disease; pressure ulcers; or epidermolysis bullosa (EB).

The wounds believed to be more susceptible to infection are chronic wounds and/or other wounds of patients who are elderly and/or who may have:
- diabetes type 1 or type 2, or
- a wound caused by an object that was dirty or contained bacteria, or
- a wound caused from a bite, or
- a wound that contains a remnant or a whole object that caused the wound, or
- a wound that is large or deep, or
- a wound that has jagged edges, or
- a wound that is chronic because by its nature a wound site is open and the patient is more likely to a patient be with a compromised immune system.

Throughout this disclosure, various quantities, such as amounts, sizes, dimensions, proportions and the like, are presented in a range format. It should be understood that the description of a quantity in range format is merely for convenience and brevity and should not be construed as an inflexible limitation on the scope of any embodiment. Accordingly, the description of a range should be considered to have specifically disclosed all the possible subranges as well as all individual numerical values within that range unless the context clearly dictates otherwise. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual values within that range, for example, 1.1, 2, 2.3, 4.62, 5, and 5.9. This applies regardless of the breadth of the range. The upper and lower limits of these intervening ranges may independently be included in the smaller ranges, and are also encompassed within the disclosure, subject to any specifically excluded limit in the stated range. Where the stated range includes one or both of the limits, ranges excluding either or both of those included limits are also included in the disclosure, unless the context clearly dictates otherwise.

The terminology used herein is for the purpose of describing particular embodiments only and is not intended to be limiting of any embodiment. As used herein, the singular forms "a," "an" and "the" are intended to include the plural forms as well, unless the context clearly indicates otherwise. It will be further understood that the terms "includes", "comprises", "including" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

Unless specifically stated or obvious from context, as used herein, the term "about" in reference to a number or range of numbers is understood to mean the stated number and numbers +/−10% thereof, or 10% below the lower listed limit and 10% above the higher listed limit for the values listed for a range.

Wound Sampling Devices

Described herein are wound sampling devices and methods of using wound sampling devices for detection of infection status of a wound. A wound sampling and infection detection device disclosed herein may be for a human or animal body. The wound sampling devices as described herein can be used as point-of-care devices for detection of infection status of a wound, which overcomes problems associated with prior art methods of determining the infection status of a wound, e.g., the need for shipment of samples to a laboratory for analysis, creating substantial delays in the detection of an infection. In some embodiments, the wound sampling device reacts with wound exudate or wound fluid to detect infection in a wound through a visible or otherwise detectable change. In some embodiments, the detectable change is a color change. In a preferred embodiment, the color is easily distinguishable from those colors that are common in wounds or body fluids.

A wound sampling device in accordance with this disclosure includes two components: (i) an indicator unit that includes a sensor tube having an open proximal end and a sensor positioned within the sensor tube, and (ii) a swab unit that includes a swab shaft having a proximal end and a distal end, a swab handle connected to the proximal end of the swab shaft and a swab tip positioned at the distal end of the swab shaft. In the embodiments shown in the Figures, the sensor is positioned at a distal end of the sensor tube; however, it is to be understood that the sensor can be positioned at other locations within the sensor tube without deviating from the inventive concepts disclosed herein. The sensor includes a substrate or a combination of substrates operable to undergo a detectable change, such as, for example, a visible color change, in response to expression of a specific infection marker present in wound fluid (such as, for example, pH). As used herein, the term "marker" or "infection marker" refers to any substance or substance feature for which detection is desired and, in some embodiments, includes a host marker, such as a biomarker, that is indicative of wound infection. The swab handle is configured to sealingly engage the open proximal end of the sensor tube in an orientation whereby the swab tip is positioned within the sensor tube. The swab shaft has a length such that, when the swab handled is engaged with the open proximal end of the sensor tube, the swab tip is adjacent to and/or in contact with the sensor within the sensor tube. With this configuration, the swab unit is operable to deliver a sample from a wound into contact with the sensor such that a health care provider can determine whether the marker is present in the fluid by determining whether the sensor has undergone a detectable change.

One embodiment of a wound sampling device in accordance with this disclosure is shown schematically in FIG. 1. Device 20 includes indicator unit 30 and swab unit 40. Indicator unit 30 includes sensor tube 32 having an open proximal end 34 and sensor 36 positioned in sensor tube 32 at a distal end 38 of sensor tube 32. Sensor 36 can be, for example, a quantity of an active substance (substrate) that undergoes a visible change when it comes into contact with a marker. The active substance can be positioned at the distal end of sensor tube 32 in a variety of manners. For example, the active substance can be coated on an inner surface of sensor tube 32 at its distal end or can be carried on a carrier material that is positioned within sensor tube 32 at its distal end. For example, a suitable carrier material can be a sized sheet of paper, cellulose, cellulose derivatives, viscose, polyamide, polyester, polyacrylate, fabric, sodium carboxymethylcellulose fibre (commercially available from ConvaTec under the trademark Hydrofibre®), cardboard, or other similar polymers that are useful as fibers, or any combination thereof. When the active substance is carried on a carrier material, the carrier material optionally can be affixed to an inner surface of sensor tube 32 or can be held in place by friction. Alternatively, the carrier material can be loosely contained within sensor tube 32. In one preferred embodiment, sensor tube 32 is composed of a transparent or translucent materials such that a visible change that occurs when sensor 36 comes into contact with a marker is detectible visually.

Swab unit 40 includes swab tip 41, swab shaft 43, and handle 45. Swab tip 41 can be formed of any suitable absorbent material and can be, for example, a flocked swab tip. In certain embodiments, swab tip 41 comprises one or more of cotton, polyurethane foam, polyester, rayon and nylon. In some instances, the absorbent swab tip comprises cellulose (for example, Lyocell), modified cellulose (for example, viscose or rayon), polyester, silk, wool, nylon, polypropylene, elastane, or mixtures thereof. In some embodiments, swab shaft 43 includes a scale, which can be, for example, engraved, embossed or printed on swab shaft 43. In some instances, the scale functions to facilitate measurement of wound depth. FIG. 1 shows device 20 with swab unit inserted only partially into indicator unit 30 to generally show the orientation of these components as would occur just prior to being connected to one another.

To use a wound sampling device disclosed herein, a fluid specimen is first collected from a wound. To briefly describe one suitable manner for collecting a fluid specimen from a wound, a health care provider swabs the wound by gently rotating the swab shaft between his or her fingers with the swab tip in contact with the wound. The swab tip is moved across the wound from margin to margin in a 10-point zigzag fashion while exerting enough pressure to express fluid from within the wound tissue. The swab unit is then affixed to the indicator unit by inserting the swab tip into the open proximal end of the sensor tube and then engaging the swab handle with the sensor tube in a manner whereby the swab tip delivers the fluid specimen into contact with the sensor.

Figure 2:
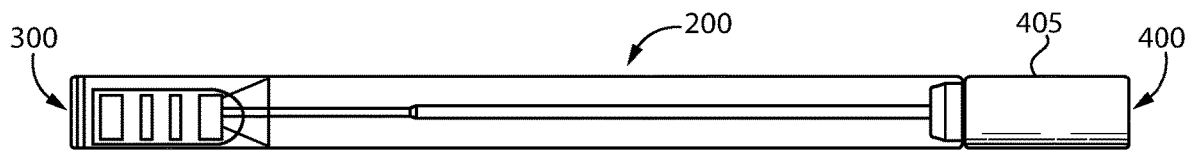
FIG. 2 illustrates a top view of a wound sampling device embodiment comprising a swab unit inserted into an indicator unit.
Figure 3:
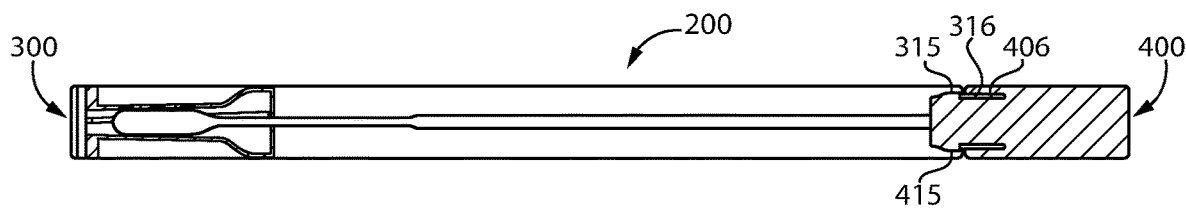
FIG. 3 illustrates a cross-sectional side view of the embodiment shown in FIG. 2.

In another embodiment, depicted in FIGS. 2-5, a variation is shown in which the indicator unit is formed of a sensor tube, a sensor, and a sensor retaining insert. For efficient manufacture, this embodiment can be constructed by providing a sensor tube that has open proximal and distal ends and positioning the sensor at the distal end of the sensor tube by affixing the sensor to a sensor retaining insert that is inserted into and sealingly affixed to the distal end of the sensor tube. In certain embodiments, the sensor retaining insert can optionally include internal ribs, struts, surfaces or other structures to guide the swab tip as it enters the sensor retaining insert to achieve a desired juxtaposition between the swab tip and the sensor. With reference to FIGS. 2-5, device 200 comprises indicator unit 300 and swab unit 400. FIG. 2 shows a side view of device 200 with swab unit 400 inserted into and connected to indicator unit 300. A cross-section of device 200 in the same orientation is shown in FIG. 3.

Figure 4:
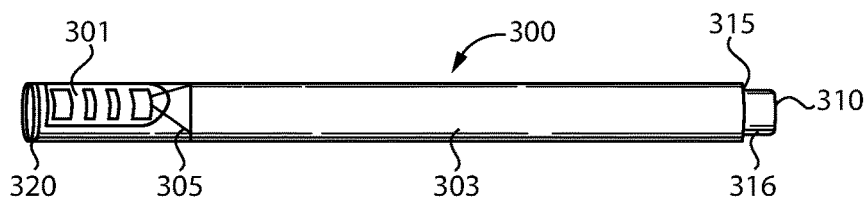
FIG. 4 illustrates a perspective view of the indicator unit of the embodiment shown in FIGS. 2 and 3.

Indicator unit 300 of device 200 is shown separated from device 200 in FIG. 4. As seen more clearly in FIG. 4, indicator unit 300 includes sensor tube 303, sensor 301 and sensor retaining insert 305. In the embodiment shown, proximal end 310 of sensor tube 303 is configured to form a shoulder 315 at which both the outer circumference of sensor tube 303 and also the lumen diameter of sensor tube 303 step down to a smaller circumference and a smaller lumen diameter respectively at segment 316 of sensor tube 303, as more clearly shown in FIG. 3. Segment 316 is sized and configured to seat within a radial channel 406 formed in handle 405 of swab unit 400. As will be discussed further below, this orientation is but one option for achieving sealing engagement of indicator unit 300 to swab unit 400 after swab unit is used to obtain a sample.

Figure 6:
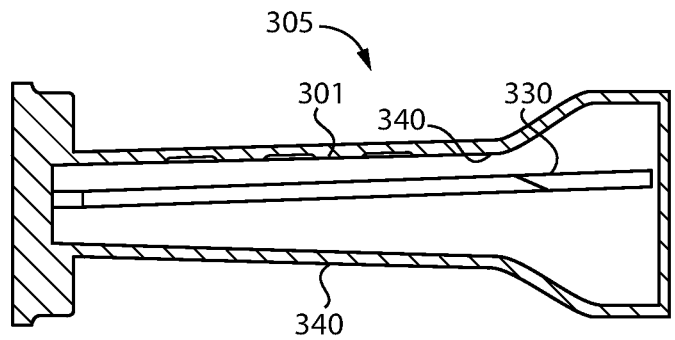
FIG. 6 illustrates a cross-sectional side view of the sensor retaining insert of the embodiment shown in FIGS. 2 and 3.

Sensor 301 and sensor retaining insert 305 are positioned at and retained within distal end 320 of sensor tube 303. Further details of sensor retaining insert 305 of this embodiment are shown in FIGS. 6-11. FIG. 6 depicts a cutaway of sensor retaining insert 305. The sensor retaining insert 305 comprises two opposing centralizing rib features 330, one of which is shown in FIG. 6, a sensor 301, and one or more inclined walls 340. Rib features 330 and inclined walls 340 guide the position of swab tip 401 as it is inserted into indicator unit 300, enabling proper spacing and alignment of swab tip 401 inside sensor retaining insert 305. The inclined walls 340 also allow for swab tip 401 to be squeezed as it comes into contact with sensor 301 and helps the transfer of fluid onto sensor 301. While this embodiment includes the described rib features and inclined walls to achieve alignment and positioning of swab tip 401 relative to sensor 301, it is to be understood that alternative structures to achieve this function are also contemplated and that such alternative structures can be substituted for the rib features 330 and/or the inclined walls 340 of this embodiment without departing from the present disclosure. For example, the sensor retaining insert, in some alternative embodiments defines an internal cavity that is conical in shape or that is tapered at a first end relative to a second end. In some embodiments, the sensor retaining insert comprises at least one protrusion on an inside surface of the sensor retaining insert. In some embodiments, the sensor retaining insert comprises at least 1, 2, 3, 4, 5, 6, 7, 8, or more than 8 protrusions on an inside surface of the sensor retaining insert. Alternatively, such structures are omitted in some embodiments. Sensor retaining insert 305 may be transparent or translucent. In some instances, sensor retaining insert 305 is a transparent molded part.

Figure 5:
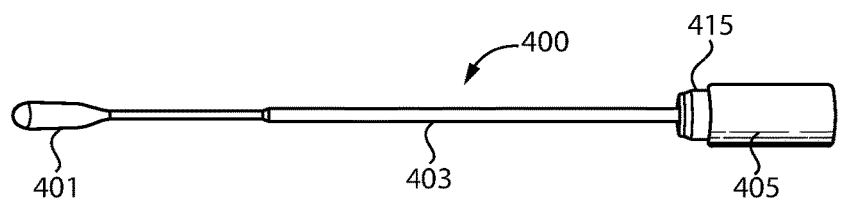
FIG. 5 illustrates the swab unit of the embodiment shown in FIGS. 2 and 3.

Swab unit 400 of device 200 is depicted in FIG. 5. Swab unit 400 includes swab tip 401, swab shaft 403, and handle 405. Swab tip 401 can be formed of any suitable absorbent material and can be, for example, a flocked swab tip. In certain embodiments, swab tip 401 comprises one or more of cotton, polyurethane foam, polyester, rayon and nylon. In some instances, the absorbent swab tip comprises cellulose (for example, Lyocell), modified cellulose (for example, viscose or rayon), polyester, silk, wool, nylon, polypropylene, elastane, or mixtures thereof. Swab shaft 403 may comprise a scale. In some instances, the scale is engraved, embossed or printed. In some instances, the scale functions to facilitate measurement of wound depth.

In some embodiments, handle 405 forms a liquid-tight and/or air-tight seal with sensor tube 303 when swab unit 400 is inserted into indicator unit 300. In some embodiments, device 200 includes features to prevent a user from separating indicator unit 300 from swab unit 400 once swab unit 401 has been inserted fully into indicator unit 300 and seated in proper position. In some embodiments, the device comprises a locking mechanism. In some embodiments, the locking mechanism comprises a one way ratchet or snap feature. In some instances, the locking mechanism comprises a luer lock or locking pins. In the embodiment depicted in FIGS. 2-11, swab unit 400 is locked once inserted into indicator unit 300 as a result of the engagement between flange 415 formed on handle 405 with shoulder 315 formed at proximal end 310 of sensor tube 303. As described above, segment 316 of sensor tube 303 is sized and configured to seat within a radial channel 406 formed in handle 405 of swab unit 400. Oriented distally to radial channel 406 is flange 415 that has a diameter greater than the lumen diameter of segment 316. Thus, when handle 405 engages distal end 310 of indicator unit 300 and is pressed to seat and seal swab unit 400 with indicator unit 300, flange 415 is deflected so that it is able to pass through the lumen of segment 315 and once flange 415 extends distally past shoulder 315, it snaps into place and engages shoulder 315 to seal swab unit 400 to indicator unit 300, as most clearly shown in FIG. 3. Flange 415 in some embodiments is a radial flange that extends around the entire circumference of handle 405. In other embodiments, flange 415 does not extend around the entire circumference of handle 405, but rather is composed of one or more smaller flanges positioned at only one or more locations around the circumference of handle 405.

The sensor tube, the sensor retaining insert, the swab shaft and the swab handle of devices as described herein may be injection molded, blow molded, or 3D printed and then assembled as described herein, or the indicator may be injection molded, blow molded, or 3D printed as a single unitary body. In some instances, the indicator unit is 3D printed. In some embodiments, the indicator unit is sterile. In some embodiments, the indicator unit is not sterile. Sensor tube 303 may be opaque. In some embodiments, sensor tube 303 is transparent. In some embodiments, sensor tube 303 is blow molded.

The sensor, the sensor tube, the sensor retaining insert, the swab shaft, and the swab handle of devices as described herein may be made of various materials. The sensor can comprise paper, cellulose, cellulose derivatives, viscose, polyamide, polyester, polyacrylate, fabric, sodium carboxymethylcellulose fibre, (commercially available from ConvaTec under the trademark Hydrofibre®), cardboard, and other similar polymers that are useful as fibers, and any combination thereof. In some instances, the sensor comprises paper. In some instances, the sensor comprises filter paper. In some instances, the sensor tube comprises polyolefin, polypropylene, polyethylene, polyurethane, polyamides, polystyrene, ethylene-vinyl alcohol (EVOH), acrylonitrile (PAN), polyvinyl chloride (PVC), or polyvinylidene chloride (PVDC), polyacrylates (e.g., (1-methyl-1,2-ethandiyl)bis[oxy(methyl-2,1-ethandiyl) diacrylate). In some instances, the sensor tube comprises polypropylene. In some instances, the sensor retaining insert comprises polyolefin, polypropylene, polyethylene, polyurethane, polyamides, ethylene-vinyl alcohol (EVOH), acrylonitrile (PAN), polyvinyl chloride (PVC), or polyvinylidene chloride (PVDC), polyacrylates (e.g., (1-methyl-1,2-ethandiyl)bis[oxy(methyl-2,1-ethandiyl) diacrylate). In some instances, the sensor retaining insert comprises polypropylene.

In some instances, the absorbent swab tip comprises non-gel-forming polymers. In some instances, the absorbent swab tip comprises cellulose (for example, Lyocell), modified cellulose (for example, viscose or rayon), polyester, silk, wool, nylon, polypropylene, elastane, or mixtures thereof.

In some instances, the absorbent swab tip comprises gel-forming polymers or sodium carboxymethylcellulose fibre (commercially available from ConvaTec under the trademark Hydrofibre®). Gel-forming polymers include, but are not limited to cellulose, carboxymethylcellulose (CMC), carboxyethylcellulose, oxidized cellulose (or a derivative thereof), cellulose ethyl sulfonate, other chemically modified cellulose, pectin, alginate, chitosan, modified chitosan, hyaluronic acid, polysaccharide, or gum-derived polymer, or any combination thereof. In some embodiments, the absorbent swab tip comprises polyvinylpyrrolidone, polyvinyl alcohols, polyvinyl ethers, polyurethanes, polyacrlyates, polyacrylamides, collagen, gelatin or mixtures thereof. In some embodiments, the absorbent swab tip comprises fibers of gel-forming polymers. In some embodiments, the absorbent swab tip comprises a nonwoven layer of gel-forming fibers. In one embodiment, the gel-forming fibers comprise sodium carboxymethylcellulose fibre.

Swab handle 405 and swab shaft 403 may comprise various materials. In some instances, swab handle 405 comprises polyolefin, polypropylene, polyethylene, polyurethane, polyamides, polystyrene, ethylene-vinyl alcohol (EVOH), acrylonitrile (PAN), polyvinyl chloride (PVC), or polyvinylidene chloride (PVDC), polyacrylates (e.g., (1-methyl-1,2-ethandiyl)bis[oxy(methyl-2,1-ethandiyl) diacrylate). In some instances, swab shaft 403 comprises polypropylene.

In some embodiments, swab tip 401 comprises a circumference that is smaller than a circumference of the sensor tube. In some embodiments, the circumference of the swab tip is at least or about 0.05, 0.06, 0.07, 0.08, 0.09, 0.1, 0.2, 0.3, 0.4, 0.5, 0.6, 0.7, 0.8, or more than 0.8 centimeters (cm). In some embodiments, a length of the swab tip is at least or about 0.5, 0.6, 0.7, 0.8, 0.9, 1, 2, 3, 4, 5, 6, 6.5, 7, 7.5, 8, or more than 8 centimeters (cm). In some embodiments, the swab shaft comprises a circumference that is smaller than a circumference of the sensor tube. In some embodiments, the circumference of the swab shaft is at least or about 0.05, 0.06, 0.07, 0.08, 0.09, 0.1, 0.2, 0.3, 0.4, 0.5, 0.6, 0.7, 0.8, or more than 0.8 centimeters (cm). In some embodiments, a length of the swab shaft is at least or about 0.5, 0.6, 0.7, 0.8, 0.9, 1, 2, 3, 4, 5, 6, 6.5, 7, 7.5, 8, 9, 10, 11, 12, 13, 14, 15, 16, 17, 18, 19, 20 or more than 20 centimeters (cm). In some embodiments, the circumference of the sensor tube is at least or about 0.06, 0.07, 0.08, 0.09, 0.1, 0.2, 0.3, 0.4, 0.5, 0.6, 0.7, 0.8, 0.9, 1, 2, 3, 4, 5, 6, or more than 6 centimeters (cm).

Sensor 301 may demonstrate a change when activated or contacted by a specific substance or condition (i.e., a marker). For example, the change can be a color change. In some embodiments, the change is a color, number, symbol, or other visible or observable marker. In some embodiments, the color change is a change from a first color to a second color, from colorless to a color, or from a color to colorless. The sensor may comprise reagents (substrates) for effecting a change. In some embodiments, reagents for effecting a change are immobilized on a carrier material. In some embodiments, the sensor comprises one or more components selected from the group consisting of enzyme-reactive indicators, reagents that are sources of peroxide, reductases, oxidases, enzymes that are able to transform color reactions, pH indicators, total protein-detecting reagents, and moisture-detecting reagents for effecting a change. In some embodiments, the reagents that are sources of peroxide are selected from peroxy acids, sodium percarbonate, and peroxide-generating oxidases, such as glucose oxidase or lactate oxidase. In some embodiments, the enzymes that are able to assist the transformation of color reactions are selected from peroxidases and laccases. In some embodiments, the enzyme-reactive indicators comprise a moiety capable of producing a visible color or detectable electronic change upon interaction with one or more target enzymes. In some embodiments, the moiety is a peroxidase substrate, arylamine, an amino phenol, an indoxyl, a neutral dye, a charged dye, a nanoparticle, a colloidal gold particle, or an analog thereof. In some embodiments, the sensor comprises a pH-sensitive moiety that presents a visible color change. In some embodiments, the pH-sensitive moiety presents a visible color change at alkaline pH. In some embodiments, the pH-sensitive moiety presents a visible color change at neutral pH. In some embodiments, the pH-sensitive moiety presents a visible color change at acidic pH. In some embodiments, the immobilized reagents comprise one or more antibody and/or antibody conjugates. In some embodiments, the immobilized reagents comprise unbound cell-surface receptors.

In some embodiments, the pH of a wound can influence many factors of wound healing, such as angiogenesis, protease activity, oxygen release, and bacterial toxicity. Chronic non-healing wounds may have an elevated alkaline environment, as do acute wounds in the early stages of healing. As a wound progresses towards healing, the pH of the wound typically moves to neutral and then becomes acidic. Monitoring of the pH of a wound may provide a method to assess the condition of the wound (e.g., infection or no infection) and aid in determining a wound's response to treatment.

In some embodiments, the pH-sensitive moiety presents a visible color change at pH=7.2-9.5. The color change is believed to be due to an evolving infection. In some embodiments, the pH-sensitive moiety presents a visible color change at pH=7.2-9.0. In some embodiments, the pH-sensitive moiety presents a visible color change at pH=7.2-8.5. In some embodiments, the pH-sensitive moiety presents a visible color change at pH=7.2-8.0. In some embodiments, the pH-sensitive moiety presents a visible color change at pH=7.5-8.5. In some embodiments, the pH-sensitive moiety presents a visible color change at pH=7.5-9.0. In some embodiments, the pH-sensitive moiety presents a visible color change at pH=8.0-9.0.

In some embodiments, the pH-sensitive moiety presents a visible color change at acidic or neutral pH. For example the pH-sensitive moiety presents a visible color change at 4.5 to about 7. A pH in this range is believed to indicate no or minimal infection. If there is minimal infection, the pH may range from 6 to 7, or 6.5 to 7.

In some embodiments, the pH-sensitive moiety is selected from bromothymol blue, phenol red, bromophenol red, chlorophenol red, thymol blue, bromocresol green, bromocresol purple; nitrazine yellow; or other sulfophthalein dyes. In one embodiment the pH-sensitive moiety has strong dark color change including for example bromocresol purple.

In some embodiments, the sensor exhibits change when it detects one or more marker, such as a biomarker. In some embodiments, the sensor exhibits change when it detects 1 marker. In some embodiments, the sensor exhibits change when it detects 2 markers. In some embodiments, the sensor exhibits change when it detects 3 markers. In some embodiments, the sensor exhibits change when it detects 4 markers. In some embodiments, the sensor exhibits change when it detects 5 markers. In some embodiments, the sensor exhibits change when it detects 6 markers. In some embodiments, the sensor exhibits change when it detects 7 markers. In some embodiments, the sensor exhibits change when it detects 8 markers. In some embodiments, the sensor exhibits change when it detects 9 markers. In some embodiments, the sensor exhibits change when it detects 10 markers. Typically, the sensor may detect one to three markers. In one embodiment the sensor may detect 2 to 5, or 2 or 3 markers; and in a further embodiment 3 markers.

In some embodiments, sensors as described herein for exhibit the change rapidly. In some instances, the change occurs in at most or about 10 seconds, 20 seconds, 30 seconds, 40 seconds, 50 seconds, 1 minute, 2 minutes, 3 minutes, 4 minutes, 5 minutes, 6 minutes, 7 minutes, 8 minutes, 9 minutes, 10 minutes.

In some embodiments, the sensor comprises a carrier material having a plurality of sections, each section comprising a substrate immobilized thereon for detection of a different marker.

Provided herein are methods for using wound sampling devices as described herein. In some embodiments, methods comprise swabbing the wound using the swab unit, inserting the swab unit inside the indicator unit, and reading a change on the sensor of the indicator unit. In some embodiments, the change is a color change. In some embodiments, inserting the swab unit into the indicator unit comprises contacting the swab tip with the sensor. In some embodiments, the change is a color, number, symbol, or other visible or observable marker. In some embodiments, the color change is a change from a first color to a second color, from colorless to a color, or from a color to colorless.

A fluid sample obtained from a wound often includes sufficient moisture to achieve a desired degree of contact between the fluid and the sensor when the swab unit is inserted into an indicator unit such that the swab tip contacts the sensor to reliably determine the presence or absence of the marker in the fluid sample. For detection of certain markers, however, delivery of a liquid, such as sterile water or other aqueous fluid to the swab tip and/or to the sensor is desirable. Liquid delivery can be achieved in accordance with certain embodiments of this disclosure by providing a reservoir of water within a chamber defined by the swab handle of a wound sampling device. In some embodiments, a liquid in the liquid chamber can be manually released. In other embodiments, the liquid in a liquid in the liquid chamber can be automatically released upon engagement of the swab unit with the indicator unit.

Figure 13:
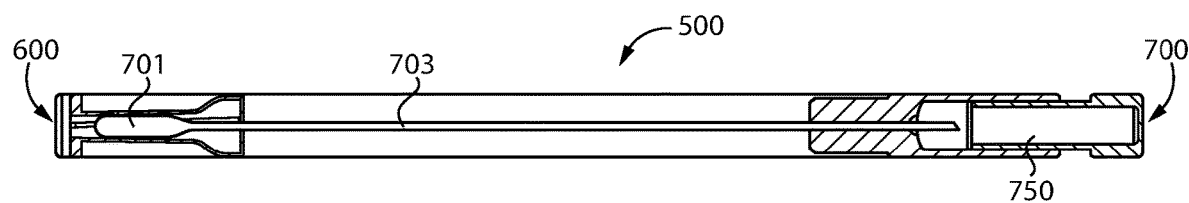
FIG. 13 illustrates a cross-sectional side view of the embodiment shown in FIG. 12.
Figure 14:
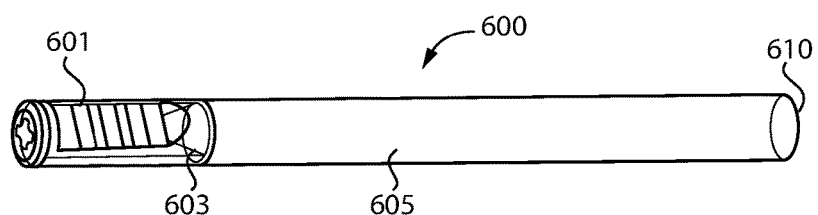
FIG. 14 illustrates a perspective view of the indicator unit of the embodiment shown in FIGS. 12 and 13.
Figure 15:
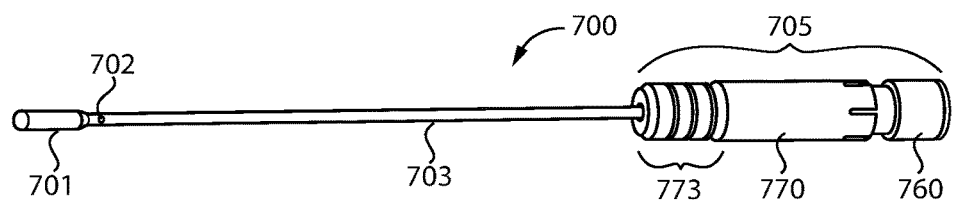
FIG. 15 illustrates a swab unit of the embodiment shown in FIGS. 12 and 13.

One such device embodiment in which a liquid in the liquid chamber can be manually released is depicted in FIGS. 12-18. Device 500 depicted in FIGS. 12 and 13 includes indicator unit 600 and swab unit 700. Swab unit 700 includes swab tip 701, swab shaft 703, and swab handle 705, wherein swab handle 705 defines liquid chamber 750. A perspective view of swab unit 700 of device 500 is shown in FIG. 15. Swab tip 701 may comprise nylon or any other absorbent material described herein. In some instances, swab tip 701 comprises cellulose (for example, Lyocell), modified cellulose (for example, viscose or rayon), polyester, silk, wool, nylon, polypropylene, elastane, or mixtures thereof. Swab shaft 703 may comprise a scale. In some embodiments, the scale is engraved or embossed. In some embodiments, the scale functions to facilitate measurement of wound depth.

Figure 12:
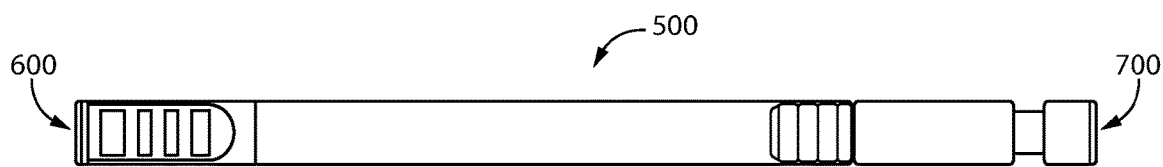
FIG. 12 illustrates a top view of yet another wound sampling device embodiment comprising a swab unit inserted into an indicator unit.

A cross-section of the device of FIG. 12 is seen in FIG. 13. Indicator unit 600 can have similar features to those described above in connection with indicator units 30, 300. In the embodiment shown, however, proximal end 610 of indicator unit 600 does not include a shoulder with stepped down outer circumference and lumen diameter, but rather includes a simple open end as shown in FIG. 14, in which indicator unit 600 includes sensor 601, sensor retaining insert 603 and sensor tube 605. In the embodiment shown, handle 705 includes a portion 773 that is configured to form a liquid-tight and/or air-tight seal with sensor tube 605 when portion 773 of swab unit 700 is inserted into proximal end 610 of indicator unit 600.

Figure 16:
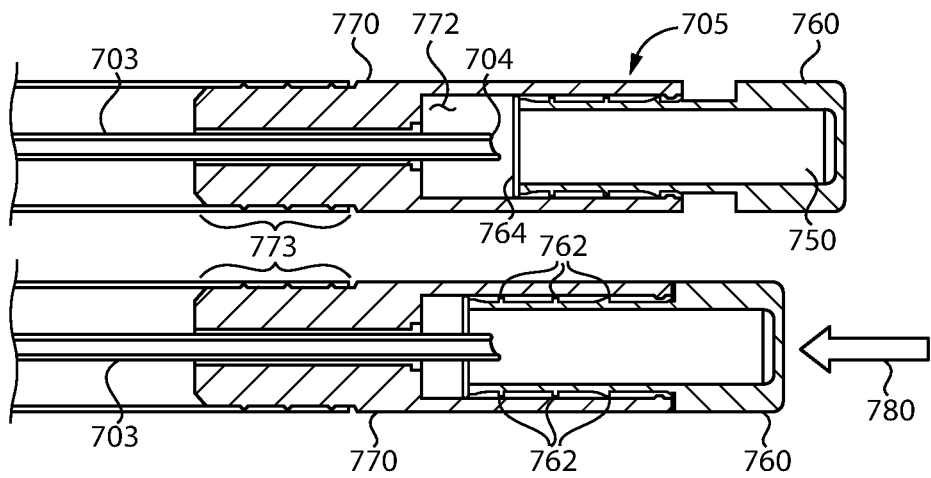
FIG. 16 illustrates a cross-sectional view of the swab unit of the embodiment shown in FIGS. 12 and 13 in the context of the proximal end of the swab shaft and inserted into the proximal end of the sensor tube.

A more detailed view of handle 705 and the relationship of handle 705 to swab shaft 703 is shown in the cross-section view of FIG. 16. Handle 705 of swab unit 700 includes a movable element 760 that is retained within, and moveable relative to, retaining element 770 of swab handle 705. Moveable element 760 defines liquid chamber 750.

Figure 17:
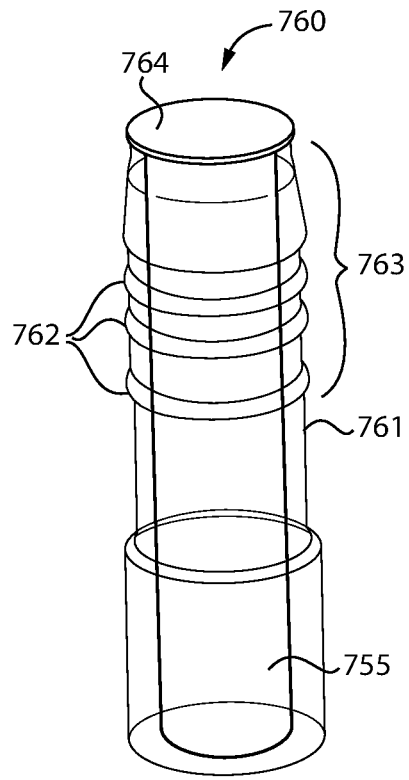
FIG. 17 illustrates construction of the movable element of the swab unit handle of the embodiment shown in FIGS. 12 and 13, also depicting the liquid chamber defined therein.

The construction of movable element 760 is shown more clearly in FIG. 17. Movable element 760 includes main body 761 which may, for example, be a molded or 3D printed plastic part, that defines external features 762 for engaging retaining element 770. Main body 761 also defines the sides and one end of internal liquid chamber 750 wherein liquid 755 is contained. The other end of liquid chamber 750 is defined by liquid chamber seal 764 that seals the open end of main body 761. Seal 764 can comprise, for example, an aluminum foil seal. Additional examples of suitable seals include, but are not limited to, other metallic foils, plastic films, membranes, ball valves, duck bill valves, other non-return valves, or combinations thereof.

Retaining element 770, which also may, for example, be a molded or 3D printed plastic part, defines a cavity 772 sized and configured to receive distal portion 763 of movable element 760. Retaining element 770 also includes distal portion 773 that is configured to be inserted into proximal end 610 of sensor tube 605. Distal portion 773 of retaining element 770 defines an axial bore through which a proximal portion of swab shaft 703 extends part way into cavity 772 in a fixed position relative to retaining element 770. Surfaces of retaining element 770 that define cavity 772 include surface features that interact with features 762 on movable element 760 to retain distal portion 763 of movable element 760 within the cavity in an un-deployed position whereby the liquid chamber seal 764 is spaced apart from proximal end 704 of swab shaft 703 until sufficient pressure is applied to movable element 760 in the direction denoted by arrow 780 in FIG. 16 to move movable element 760 in a distal direction to deploy the liquid contained in liquid chamber 755.

In device 500, swab shaft 703 is formed as a hollow tube that has an open proximal end 704 and that defines a small aperture 702 near swab tip 701 that is in fluid communication with the lumen of swab shaft 703. In the embodiment shown, proximal end 704 of swab shaft 703 defines a sharpened edge that operates to breach liquid chamber seal 764 when movable element 760 is moved as described above. Breaching of liquid chamber seal 764 by proximal end 704 of swab shaft 703 causes proximal end 704 to enter liquid chamber 750, which enables the liquid contained therein to enter the lumen of hollow shaft 703 and flow distally toward, and then through, aperture 702 where the liquid wets swab tip 701 and/or sensor 601 positioned in contact with swab tip 701.

Figure 18:
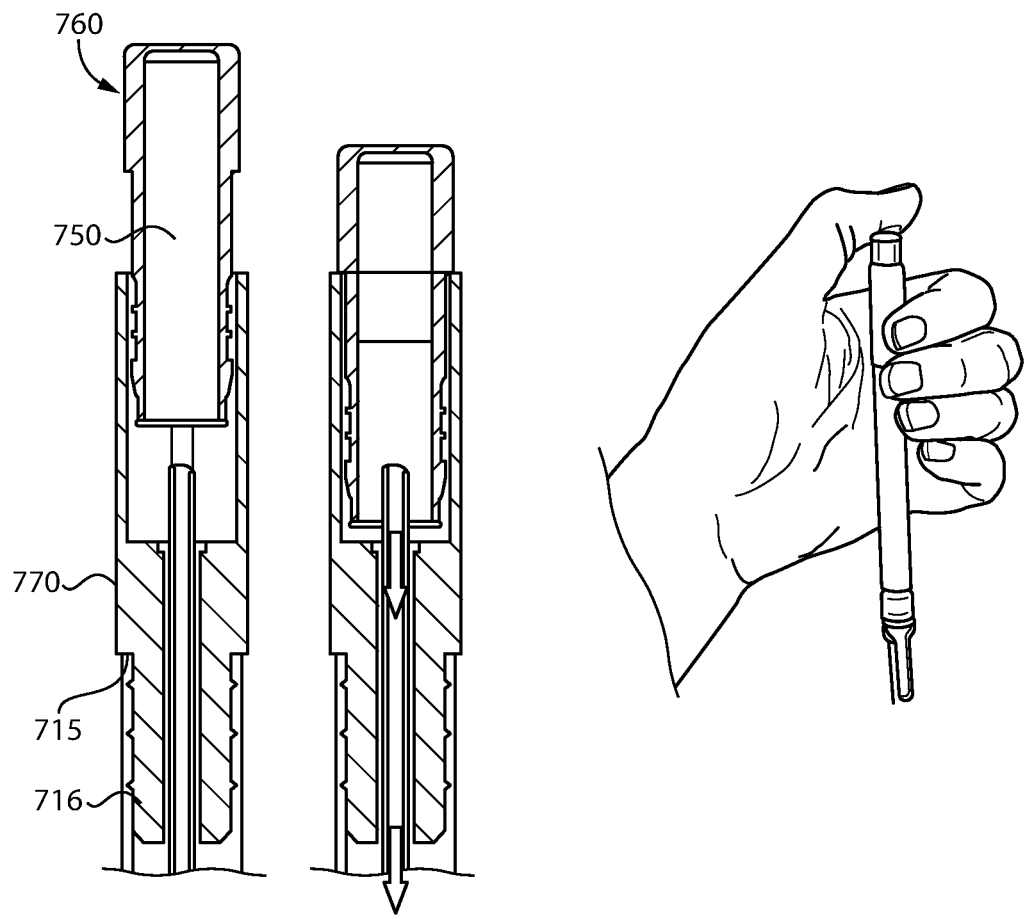
FIG. 18 illustrates deployment of a liquid from the liquid chamber.

FIG. 18 shows use of device 500. In some instances, surface structures 762 on distal portion 763 of movable element 760 and surface features on surfaces of retaining element 770 that define cavity 772 engage one another to prevent movable element 760 from being pulled out of cavity 772. In some instances, movable element 760 is configured to slide within cavity 772 of retaining element 770 when pressed. When movable element 760 of the device is pressed, proximal end 704 of swab shaft 703 contacts liquid chamber seal 764 and ruptures seal 764, thereby releasing the liquid through the lumen of swab shaft 703, through aperture 702 and into sensor tube 605 where the liquid can contact swab tip 701 and/or sensor 601. Swab unit 700 can be locked once inserted into the indicator unit. In some embodiments, the locking mechanism comprises a one way ratchet or snap feature. Moreover, moveable element 760 can be locked once it is moved to its compressed position by operation of the surface structures 762 on distal portion 763 of movable element 760 and surface features on surfaces of retaining element 770 that define cavity 772.

In alternate embodiments, swab shaft 703 extends to or into cavity 772 and operates as a conduit for liquid to travel from liquid chamber 750 to swab tip 701 and/or sensor 601, but does not operate to pierce liquid chamber seal 764. In such embodiments, other piercing structures can be affixed to retaining element 770 within cavity 772 to pierce liquid chamber seal 764 when movable element 760 is manually compressed.

While one example of manually delivering a liquid into the sensor tube is described in detail herein, a wide variety of alternative structures are contemplated for manually delivering a liquid from the handle of a swab unit into the sensor tube. For example, in some embodiments (not shown), the handle comprises a piercing member and a plunger to not only pierce the liquid seal, but also to compress the liquid and propel it into sensor tube 605. In some embodiments, when the movable element is pressed downward, a piercing member is released to pierce the seal via a spring loaded mechanism or other arrangement.

In some embodiments, methods for using wound sampling devices as described herein comprise swabbing the wound using the swab unit, inserting the swab unit inside the indicator unit, manually releasing liquid from the liquid chamber into the sensor tube, and reading the device or sensor for a change. In some embodiments, inserting the swab unit into the indicator unit comprises contacting the sensor with the swab. In some embodiments, the change is a color change. In some embodiments, the change is a color, number, symbol, or other visible or observable marker. In some embodiments, the color change is a change from a first color to a second color, from colorless to a color, or from a color to colorless. In some embodiments, releasing the liquid comprises pressing a movable member to pierce a seal on the liquid chamber.

Figure 19:
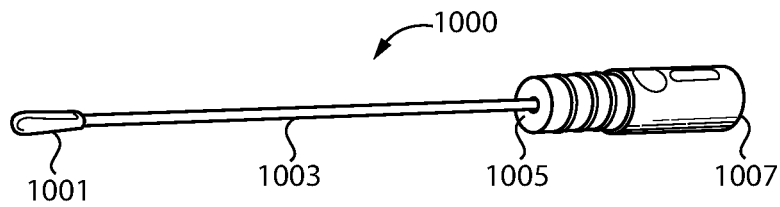
FIG. 19 illustrates a swab unit of still another wound sampling device embodiment that enables auto deployment of a liquid from a liquid chamber upon insertion of swab unit into an indicator unit.
Figure 20:
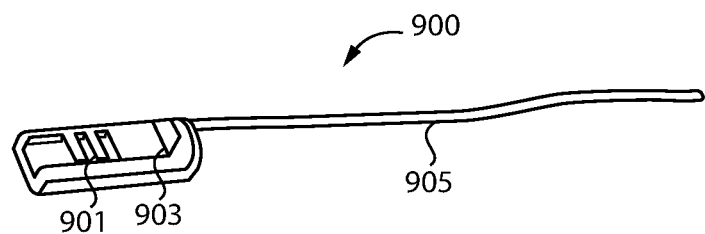
FIG. 20 illustrates an indicator unit of the wound sampling embodiment that enables auto deployment of a liquid from a liquid chamber upon insertion of a swab unit into the indicator unit.

With reference to FIGS. 19-27, another embodiment of a wound sampling device 800 in accordance with this disclosure that is operable to deliver water to the swab tip and/or to the sensor device includes indicator unit 900 and swab unit 1000 which has handle 1007 defining a liquid chamber and configured for auto deployment of liquid when swab unit 1000 is seated in indicator unit 900. FIG. 19 depicts swab unit 1000 for device 800. Swab unit 1000 includes swab tip 1001, swab shaft 1003, liquid chamber seal 1005, and swab handle 1007 defining liquid chamber 1050. Swab tip 1001 may comprise nylon or other absorbent material as described herein. In some instances, swab tip 1001 comprises cellulose (for example, Lyocell), modified cellulose (for example, viscose or rayon), polyester, silk, wool, nylon, polypropylene, elastane, foam or mixtures thereof.

Figure 21:
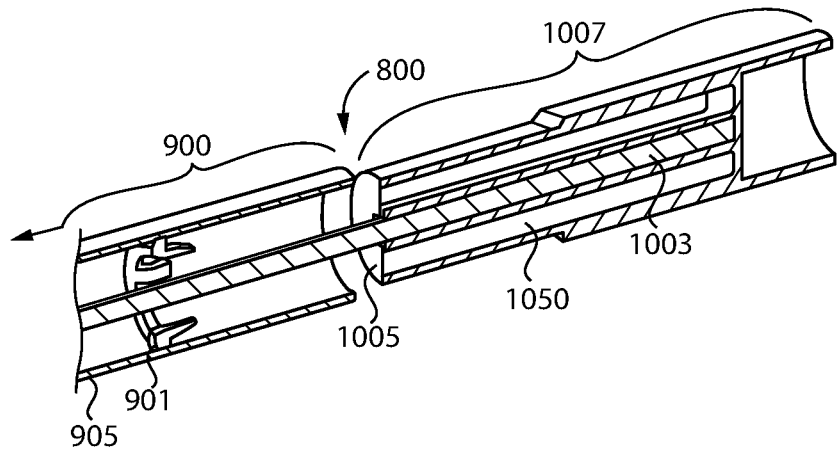
FIGS. 21-24 illustrate cross-sectional views of the swab unit shown in FIG. 19 and the distal end of the indicator unit shown in FIG. 20 in various stages of engagement.
Figure 22:
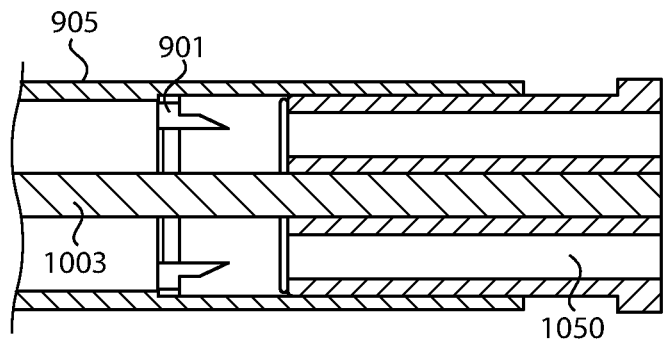
Figure 23:
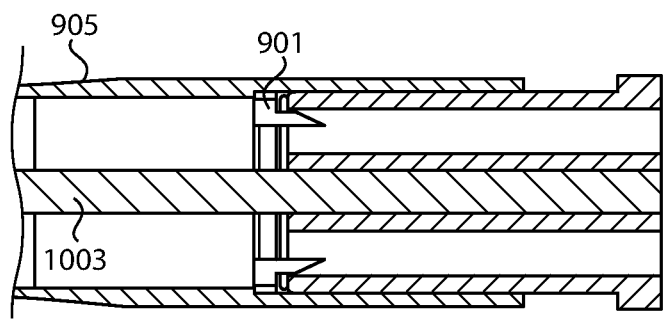
Figure 24:
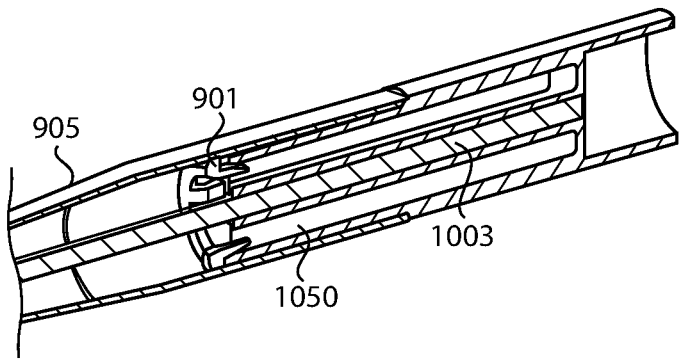

Cross-sections showing various features of device 800 are provided in FIGS. 21-24. FIG. 21 shows a cross-section of device 800 comprising sensor tube 905, piercing ring 901 affixed to sensor tube 905, liquid chamber seal 1005, which forms an end of liquid chamber 1050 that contains a sterile liquid, swab shaft 1003, and handle 1007. FIG. 22 shows a zoomed-in image of the proximal end of device 800. Handle 1007 of swab unit 1000 forms a liquid-tight and/or air-tight seal with sensor tube 905 of indicator unit 900 when swab unit 900 is inserted into sensor tube 905.

Figure 25:
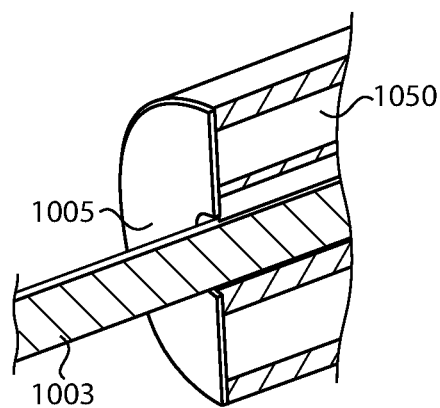
FIG. 25 illustrates a zoomed-in cross-sectional image of a portion of the swab unit shown in FIG. 19.
Figure 26:
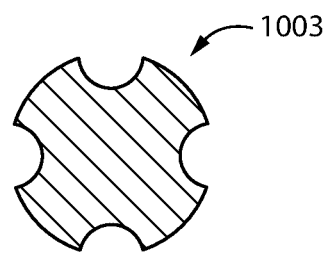
FIG. 26 illustrates a cross-section of the swab shaft of the swab unit shown in FIG. 19.
Figure 27:
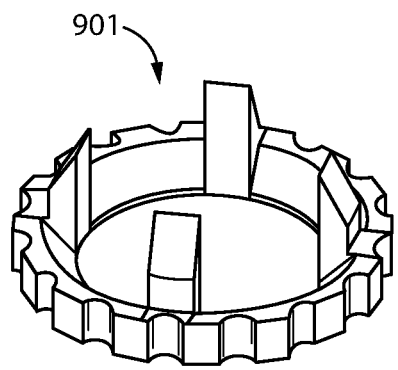
FIG. 27 illustrates a piercing ring of the indicator unit shown in FIG. 20.

FIGS. 25-26 show cross-sectional views of parts of device 800 and FIG. 27 shows a perspective view piercing ring 901. Device 800 comprises a seal 1005 and a swab shaft cross-section 1003 having a shape as seen in FIG. 26. In alternate embodiments, the cross-section shape is a triangle, square, circle, oval, or star. In some instances, the cross-section shape of swab shaft 1003 is configured to enhance the flow of liquid from the liquid chamber along the swab shaft after the seal is pierced or opened, allowing the liquid to flow from liquid chamber 1050 to swab tip 1001, thereby wetting swab tip 1001 and/or sensor 901. Examples of suitable seals include, but are not limited to, a foil, a ball valve, a film, a membrane, a duck bill valve, or other non-return valve.

The swab unit for use with devices as described herein can comprise a handle that comprises features (not shown) for allowing the swab to rotate when being inserted inside the indicator unit. In some instances, the features are helical features, such as threads. In some instances, the features allow for transfer of fluid to the sensor.

An upper edge of piercing ring 901 includes at least one sharp piercing edge that contacts and pierces liquid chamber seal 1005 when swab unit 1000 is inserted into indicator unit 900.

The liquid chamber can be any shape, including a cylinder. In some embodiments, the liquid chamber 1207 surrounds a void configured to accept an end of the swab shaft 1209. In some of such embodiments, the handle is affixed to the swab shaft inserted into the void.

With respect to the embodiments that deliver liquid into the sensor tube, in some embodiments, the liquid is water. In other embodiments, the liquid is a buffer. The buffer may comprise enzymes, salts, or substrates. An amount of fluid may include at least or about 500 uL, 1 mL, 1.5 mL, 2 mL, 2.5 mL, 3 mL, 3.5 mL, 4 mL, 5 mL, or more than 5 mL. In some instances, the amount of fluid is in a range of about 500 uL to about 5 mL, 1 mL to about 4 mL, about 1.5 mL to about 3.5 mL, or about 2 mL to about 3 mL.

The sensor may comprise one or more components selected from the group consisting of enzyme-reactive indicators, reagents that are sources of peroxide, enzymes that are able to transform color reactions, pH indicators, total protein-detecting reagents, and moisture-detecting reagents. The change may indicate treatment of wounds, diagnose wounds, monitor the condition of a wound, the healing process, or detect markers of infection in wounds.

In some instances, methods for using wound sampling devices as described herein comprise swabbing the wound using the swab unit, inserting the swab unit inside the indicator unit, automatically releasing liquid from the liquid chamber into the sensor tube, and reading the device or sensor for a change. In some embodiments, the indicator unit comprises a piercing member. In some embodiments, the seal is pierced to release the liquid in the liquid chamber. In some embodiments, the seal is pierced when the swab unit is inserted in the indicator unit. For example, the seal is pierced when the swab unit is pressed in the indicator unit and contact between the swab unit and the indicator unit thereby punctures the seal. In some embodiments, when the swab unit is inserted into the indicator unit, a piercing ring or other piercing element ruptures a liquid chamber seal and the liquid is discharged. In some embodiments, inserting the swab unit into the indicator unit comprises contacting the sensor with the swab. In some embodiments, the change is a color change. In some embodiments, the change is a color, number, symbol, or other visible or observable marker. In some embodiments, the color change is a change from a first color to a second color, from colorless to a color, or from a color to colorless.

In some embodiments, the swab unit handle, or a portion of the swab unit handle, is pushed into the indicator unit and rotated to lock into the tube. The swab unit handle may be rotated by at least or about 5°, 10°, 15°, 20°, 25°, 30°, 35°, 40°, 45°, 50°, 55°, 60°, 70°, 80°, 90°, 100°, 120°, 140°, 160°, 180°, 200°, 220°, 240°, 260°, 280°, 300°, 320°, 340°, or 360° until the indicator unit is locked. In some embodiments, the swab unit handle is rotated by more 360° until the indicator unit is locked In other embodiments, the swab unit handle is not pushed into the indicator unit, but rather the swab unit is sealingly attached to the indicator unit in an appropriate orientation using a different attachment mechanism. In some cases, locking the handle in or to the indicator unit forms an air-tight and/or liquid-tight seal between the handle and the indicator unit. This seal can serve to retain any liquid or sample inside of the sealed device.

Methods of Use

In some embodiments, devices and methods as described herein are used to indicate an infection status of a wound, e.g., to indicate whether a wound is infected. In some embodiments, devices and methods disclosed herein detect biological markers or targets from body fluid that are known to be associated with, or indicators of, infection. In some embodiments, the body fluid is blood, plasma, serum, cerebrospinal fluid, sputum, urine or wound exudate. In some embodiments, the body fluid is wound exudate. In some embodiments, the devices and methods as described herein are used to diagnose chronic wounds. In some embodiments, devices and methods as described herein are used to indicate need for treatment of chronic wounds. In some embodiments, devices and methods as described herein are used to indicate need for treatment of surgical or acute wounds. In some embodiments, devices and methods as described herein are used to monitor the condition of a wound or surgical site and its healing process or status. In some embodiments, devices and methods as described herein are used to detect the pH and/or presence of markers of infection in wounds.

Methods for using wound sampling devices as described herein may be used to detect wound markers. For example, markers for the wound healing process are detected using devices as described herein. Detection of wound markers may be indicated by a visible change. In some embodiments, the visible change is a color. In some embodiments, the color is selected from dark blue, dark green, and black. It is clear to those skilled in the art that the signal effect of the color change depends on context and practical consideration of interfering colors form the wound itself. In some embodiments, the visible change is fluorescent, luminescent, or mediated by physical means such as electrical, refraction, gas evolution or polymer state change.

In some embodiments, the wound markers are host markers in the wound fluid. As used herein the term host means patient or animal having the wound. For example, devices and methods as described herein comprise one or more chemical substrates that react with host biomarkers in the wound fluid, such as substrates that react with myeloperoxidase (MPO), peroxidase, elastase, lysozyme, protease, cathepsin G, catalase, lipase, or esterase in the wound fluid.

In some embodiments, a microbial infection is detected via host immune response using devices as described herein. Examples of microorganisms that may induce a host immune response include, but are not limited to, bacteria, yeast, fungi (which may also be described as mold), and viruses. In one embodiment, the micro-organisms may be gram negative bacteria (e.g. *Escherichia coli, Pseudomonas aeruginosa, Klebsiella pneumoniae, Bacteroides* spp). In another embodiment the micro-organisms may be gram positive bacteria (e.g. *Staphylococcus* spp, *Streptococcus* spp, *Clostridium* spp, *Peptostreptococcus* spp). In one embodiment the micro-organisms may be a combination of gram positive and gram negative bacteria. In one embodiment, the micro-organisms may be a combination of aerobic and anaerobic bacteria.

EXAMPLES

The following examples are given for the purpose of illustrating various embodiments of the invention and are not meant to limit the present invention in any fashion. The present examples, along with the methods described herein are presently representative of preferred embodiments, are provided only as examples, and are not intended as limitations on the scope of the invention. Changes therein and other uses which are encompassed within the spirit of the invention as defined by the scope of the claims will occur to those skilled in the art.

Example 1: Indicator Tube and Swab Handle

Figure 7:
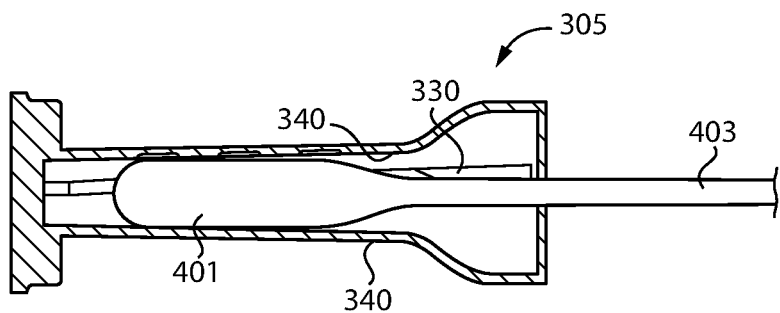
FIG. 7 illustrates a cross-sectional side view of the swab tip inserted into the sensor retaining insert of the indicator unit of the embodiment shown in FIGS. 2 and 3.
Figure 8:
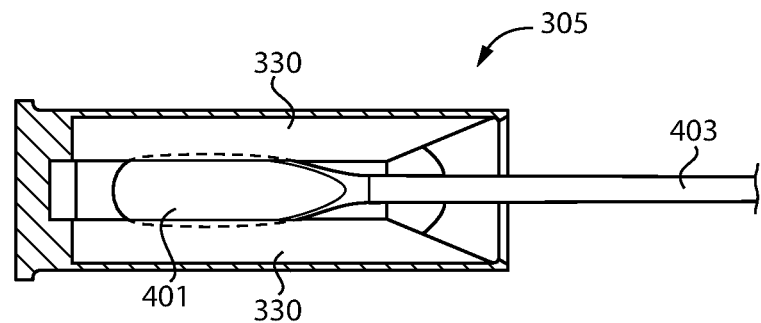
FIG. 8 illustrates a cross-sectional top view of the swab tip inserted into the sensor retaining insert of the indicator unit of the embodiment shown in FIGS. 2 and 3.
Figure 9:
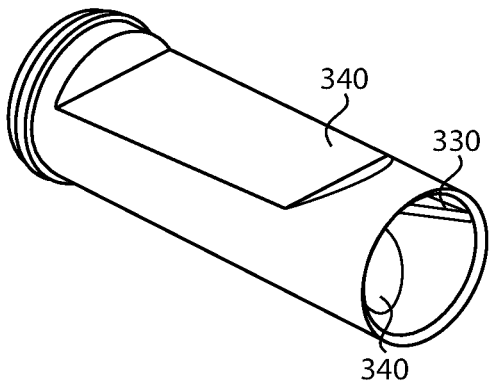
FIG. 9 illustrates a perspective view of the sensor retaining insert of the embodiment shown in FIGS. 2 and 3.
Figure 10:
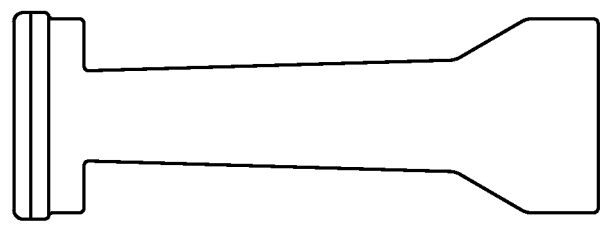
FIG. 10 illustrates a side view of the sensor retaining insert of the embodiment shown in FIGS. 2 and 3.
Figure 11:
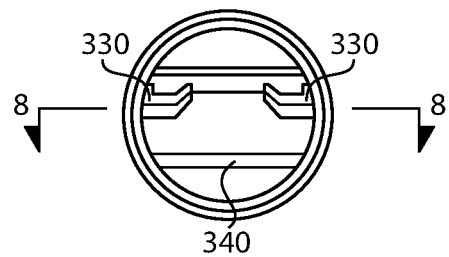
FIG. 11 illustrates an end view of the sensor retaining insert of the embodiment shown in FIGS. 2 and 3.

Device 200 shown in FIGS. 2-3 and described herein is used by swabbing a wound with absorbent swab tip 401 of swab unit 400 followed by insertion of swab unit 400 into the indicator unit 300. The device may contact body fluid such as blood, plasma, serum, cerebrospinal fluid, sputum, urine or wound exudate. Absorbent swab tip 401 then makes contact with sensor 301 in sensor retaining insert 305. The sensor retaining insert may comprise an inclined wall feature as seen in FIGS. 6-8 such that when the swab shaft is inserted into the indicator tube, the inclined wall feature allows for a substance, such as a fluid or an exudate, on the absorbent swab tip to be squeezed and transferred to the sensor.

Following transfer of fluid from the swab shaft onto the sensor, a change is read. The change may be read after 30 seconds. In some instances, the change is read at most after 5 minutes. The change may be a color change. In some instances, the change is a color, number, symbol, or other visible or observable marker. The sensor may comprise one or more components selected from the group consisting of enzyme-reactive indicators, reagents that are sources of peroxide, enzymes that are able to transform color reactions, pH indicators, total protein-detecting reagents, and moisture-detecting reagents. The change may indicate treatment of wounds, diagnose wounds, monitor the condition of a wound, the healing process, or detect markers of infection in wounds.

Example 2: Indicator Tube and Swab Handle with Liquid Chamber for Manual Deployment Device 500 shown in FIGS. 12-13 and described herein is used by swabbing a wound with absorbent swab tip 701 of swab unit 700 followed by insertion of swab unit 800 into indicator unit 700. The device may contact body fluid such as blood, plasma, serum, cerebrospinal fluid, sputum, urine or wound exudate. Movable element 760 is then pressed for liquid deployment. When the movable element of the device is pressed, the proximal end of swab shaft 703 ruptures the liquid chamber seal and liquid is delivered at the swab tip.

Following transfer of fluid from the swab shaft onto the sensor, a change is read. The change may be read after 30 seconds. In some instances, the change is read at most after 5 minutes. The change may be a color change. In some instances, the change is a color, number, symbol, or other visible or observable marker. The sensor may comprise one or more components selected from the group consisting of enzyme-reactive indicators, reagents that are sources of peroxide, enzymes that are able to transform color reactions, pH indicators, total protein-detecting reagents, and moisture-detecting reagents. The change may indicate treatment of wounds, diagnose wounds, monitor the condition of a wound, the healing process, or detect markers of infection in wounds.

Example 3: Indicator Tube and Swab Handle with Liquid Chamber for Automatic Deployment The device 800 shown in FIGS. 19-27 and described herein is used by swabbing a wound with absorbent swab tip 1001 of swab unit 1000 followed by insertion of swab unit 1000 into indicator unit 900. The device may contact body fluid such as blood, plasma, serum, cerebrospinal fluid, sputum, urine or wound exudate. Absorbent swab tip 1001 then makes contact with the sensor 901. Liquid is discharged automatically. When the swab unit is inserted into the indicator tube, the piercing ring ruptures the liquid chamber seal and the liquid is discharged. See FIGS. 21-24.

Following transfer of fluid from the swab shaft onto the sensor, a change is read. The change may be read after 30 seconds. In some instances, the change is read at most after 5 minutes. The change may be a color change. In some instances, the change is a color, number, symbol, or other visible or observable marker. The sensor may comprise one or more components selected from the group consisting of enzyme-reactive indicators, reagents that are sources of peroxide, enzymes that are able to transform color reactions, pH indicators, total protein-detecting reagents, and moisture-detecting reagents. The change may indicate treatment of wounds, diagnose wounds, monitor the condition of a wound, the healing process, or detect markers of infection in wounds.

As will be appreciated from the descriptions herein and the associated Figures, a wide variety of aspects and embodiments are contemplated by the present disclosure, examples of which include, without limitation, the aspects and embodiments listed below:

A device for detecting an infection in a wound that includes an indicator unit and a swab unit, wherein the indicator unit comprises a sensor tube having an open proximal end and a sensor positioned in the sensor tube, and wherein the swab unit comprises a swab shaft having a proximal end and a distal end, a swab tip positioned at the distal end of the swab shaft, and a swab handle connected to the swab shaft at the proximal end of the swab shaft, the swab handle being configured to sealingly engage the open proximal end of the sensor tube.

A method for detecting a marker in a wound that includes (a) contacting the wound with the swab tip of a device in accordance with any device embodiment disclosed herein, (b) inserting the swab tip inside the sensor tube and sealingly engaging the swab unit to the indicator unit, and (c) observing a change in the sensor.

A device or method in accordance with any other embodiment disclosed herein, wherein the sensor comprises a carrier material and at least one substrate that is operable to undergo a visible color change in response to expression of a specific infection marker present in wound fluid A device or method in accordance with any other embodiment disclosed herein, wherein the sensor comprises at least two substrates, each substrate operable to undergo a visible color change in response to expression of a different marker present in wound fluid.

A device or method in accordance with any other embodiment disclosed herein that includes a carrier material, wherein the carrier material comprises at least one material selected from the group consisting of paper, cellulose, cellulose derivatives, viscose, polyamide, polyester, polyacrylate, fabric, sodium carboxymethylcellulose fiber, and cardboard.

A device or method in accordance with any other embodiment disclosed herein, wherein the indicator unit further comprises a sensor retaining insert sealingly engaged to a distal end of the sensor tube, and wherein the sensor is affixed to the sensor retaining insert.

A device or method in accordance with any other embodiment disclosed herein that includes a sensor retaining insert, wherein the sensor retaining insert defines a cavity configured to receive the swab tip when the swab unit is sealingly engaged to the indicator unit.

A device or method in accordance with any other embodiment disclosed herein that includes a sensor retaining insert and defines a cavity configured to receive the swab tip when the swab unit is sealingly engaged to the indicator unit, wherein the sensor retaining insert comprises at least one structural feature in or adjacent to the cavity to guide the swab tip as it enters the sensor retaining insert into a desired juxtaposition with the sensor.

A device or method in accordance with any other embodiment disclosed herein that includes at least one structural feature to guide the swab tip as it enters the sensor retaining insert wherein the at least one structural feature is selected from rib features, inclined cavity walls and combinations thereof.

A device or method in accordance with any other embodiment disclosed herein, wherein the swab tip comprises cellulose, modified cellulose, polyurethane foam, polyester, silk, wool, nylon, polypropylene, elastane, or mixtures thereof.

A device or method in accordance with any other embodiment disclosed herein, wherein the sensor comprises a member selected from the group consisting of an enzyme-reactive indicator, a reagent that is a source of peroxide, an enzyme that is able to transform color reactions, a pH indicator, a total protein-detecting reagent, a moisture-detecting reagent and combinations thereof.

A device or method in accordance with any other embodiment disclosed herein that includes a pH indicator, wherein the pH indicator comprises a pH-sensitive reagent.

A system or method in accordance with any other embodiment disclosed herein that includes an enzyme-reactive indicator, wherein the enzyme-reactive indicator comprises a moiety capable of producing a visible color or detectable electronic change upon interaction with one or more target enzymes.

A device or method in accordance with any other embodiment disclosed herein that includes an enzyme-reactive indicator comprising a moiety capable of producing a visible color or detectable electronic change, wherein the moiety is selected from the group consisting of a peroxidase substrate, arylamine, an amino phenol, an indoxyl, a neutral dye, a charged dye, a nanoparticle, a colloidal gold particle, and combinations or analogs thereof.

A device or method in accordance with any other embodiment disclosed herein, wherein the swab handle defines a liquid chamber and wherein the swab handle in operable to contain a liquid in the liquid chamber and release the liquid into the sensor tube after the swab tip is positioned within the sensor tube.

A device or method in accordance with any other embodiment disclosed herein that includes a swab handle defining a liquid chamber, wherein the swab handle is configured for manual release of the liquid from the liquid chamber.

A device or method in accordance with any other embodiment disclosed herein, wherein the swab handle comprises a retaining element configured to attach to the sensor tube, the retaining element defining a cavity, and a movable element retained within the cavity and movable relative to the retaining element.

A device or method in accordance with any other embodiment disclosed herein, wherein the liquid chamber is contained within the movable element.

A device or method in accordance with any other embodiment disclosed herein, wherein the movable element further comprises a liquid chamber seal, wherein the handle further comprises a piercing member fixedly attached to the retaining element, and wherein moving the movable element from a proximal position to a distal position causes the piercing member to pierce the liquid chamber seal to release the liquid into the sensor tube.

A device or method in accordance with any other embodiment disclosed herein, wherein the seal comprises a member selected from the group consisting of a metallic foil and a plastic film.

A device or method in accordance with any other embodiment disclosed herein, wherein the swab shaft is fixedly attached to the retaining element such that a proximal end of the swab shaft extends into the cavity, and wherein the piercing member comprises the proximal end of the swab shaft.

A device or method in accordance with any other embodiment disclosed herein, wherein the swab shaft comprises a tube defining a longitudinal passageway therethrough, and wherein, after the liquid chamber seal is pierced, the liquid chamber is in fluid communication with the sensor tube through the passageway.

A device or method in accordance with any other embodiment disclosed herein, wherein the swab shaft defines a radial aperture at its distal end near the swab tip, and wherein, after the liquid chamber seal is pierced, the liquid chamber is in fluid communication with the sensor tube through the passageway and the aperture.

A device or method in accordance with any other embodiment disclosed herein, further comprising a locking mechanism that is operable to prevent the movable element from moving in a proximal direction after the liquid chamber seal is pierced.

A device or method in accordance with any other embodiment disclosed herein, wherein the swab handle is configured for automatic release of the liquid from the liquid chamber when the handle of the swab unit is sealingly engaged to the open proximal end of the sensor tube.

A device or method in accordance with any other embodiment disclosed herein, wherein the swab handle comprises a liquid chamber seal positioned at a distal end of the liquid chamber, wherein the indicator unit further comprises a piercing member fixedly attached to the sensor tube at a location whereby the piercing member contacts the liquid chamber seal only when the distal end is inserted into the sensor tube, and wherein inserting the distal end into the sensor tube causes the piercing member to pierce the liquid chamber seal to release the liquid into the sensor tube.

A device or method in accordance with any other embodiment disclosed herein, wherein the piercing member is a piercing ring.

A device or method in accordance with any other embodiment disclosed herein, wherein the liquid chamber contains a liquid in an amount of about 500 uL, 1 mL, 1.5 mL, 2 mL, 2.5 mL, 3 mL, 3.5 mL, or 4 mL.

A method in accordance with any other method disclosed herein, wherein the marker is a host biomarker.

A method in accordance with any other embodiment disclosed herein, wherein the change is a color change, a fluorescent signal, a luminescent signal, or an electrical change.

A method in accordance with any other embodiment disclosed herein, wherein the sensor comprises a carrier material and at least one substrate that is operable to undergo a visible color change in response to expression of a specific infection marker present in wound fluid released from the swab tip.

A method in accordance with any other embodiment disclosed herein, further comprising (d) comparing the signal to a reference or a control to determine a level of the marker.

A method in accordance with any other embodiment that includes a movable element disclosed herein, further comprising pressing the movable element following step (b).

A method in accordance with any other embodiment disclosed herein, wherein step (b) comprises placing the swab tip of the swab unit in contact with the sensor of the indicator unit.

A method in accordance with any other embodiment disclosed herein, wherein step (b) results in piercing of a liquid seal.

A method in accordance with any other embodiment disclosed herein, wherein the piercing of the liquid seal releases liquid into the sensor tube.

While embodiments of the present disclosure have been shown and described herein, it is to be understood by those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What we claim is:

1. A device for detecting an infection in a wound, comprising:
   a) an indicator unit; wherein the indicator unit comprises:
      i. a sensor tube having an open proximal end; and
      ii. a sensor positioned in the sensor tube; and
   b) a swab unit, wherein the swab unit comprises:
      i. a swab shaft having a proximal end and a distal end;
      ii. a swab tip positioned at the distal end of the swab shaft; and
      iii. a swab handle connected to the swab shaft at the proximal end of the swab shaft, the swab handle being configured to sealingly engage the open proximal end of the sensor tube, the swab handle comprising (i) a retaining element that defines a cavity and attaches to the sensor tube, (ii) a moveable element retained within the cavity and moveable relative to the retaining element, the moveable element comprising a liquid chamber and a liquid chamber seal that retains liquid within the liquid chamber, and (iii) a piercing member fixedly attached to the retaining element, movement of the moveable element from a proximal position to a distal position causing the piercing member to pierce the liquid chamber seal to release the liquid into the sensor tube.

2. The device of claim 1, wherein the sensor comprises a carrier material and at least one substrate that is operable to undergo a visible color change in response to expression of a specific infection marker present in wound fluid.

3. The device of claim 2, wherein the sensor comprises at least two substrates, each substrate operable to undergo a visible color change in response to expression of a different marker present in wound fluid.

4. The device of claim 2, wherein the carrier material comprises at least one material selected from the group consisting of paper, cellulose, cellulose derivatives, viscose, polyamide, polyester, polyacrylate, fabric, sodium carboxymethylcellulose fiber, and cardboard.

5. The device of claim 1, wherein the indicator unit further comprises a sensor retaining insert sealingly engaged to a distal end of the sensor tube, and wherein the sensor is affixed to the sensor retaining insert.

6. The device of claim 5, wherein the sensor retaining insert defines a cavity configured to receive the swab tip when the swab unit is sealingly engaged to the indicator unit.

7. The device of claim 5, wherein the sensor retaining insert comprises at least one structural feature in or adjacent to the cavity to guide the swab tip as it enters the sensor retaining insert into a desired juxtaposition with the sensor.

8. The device of claim 7, wherein the at least one structural feature is selected from rib features, inclined cavity walls and combinations thereof.

9. The device of claim 1, wherein the swab tip comprises cellulose, modified cellulose, polyurethane foam, polyester, silk, wool, nylon, polypropylene, elastane, or mixtures thereof.

10. The device of claim 1, wherein the sensor comprises a member selected from the group consisting of an enzyme-reactive indicator, a reagent that is a source of peroxide, an enzyme that is able to transform color reactions, a pH indicator, a total protein-detecting reagent, a moisture-detecting reagent and combinations thereof.

11. The device of claim 10, wherein the sensor comprises the pH indicator, and wherein the pH indicator comprises a pH-sensitive reagent.

12. The device of claim 10, wherein the sensor comprises the enzyme-reactive indicator, and wherein the enzyme-reactive indicator comprises a moiety capable of producing a visible color or detectable electronic change upon interaction with one or more target enzymes.

13. The device of claim 12, wherein the moiety is selected from the group consisting of a peroxidase substrate, arylamine, an amino phenol, an indoxyl, a neutral dye, a charged dye, a nanoparticle, a colloidal gold particle, and combinations or analogs thereof.

14. The device of claim 1, wherein the seal comprises a member selected from the group consisting of a metallic foil and a plastic film.

15. The device of claim 1, wherein the swab shaft is fixedly attached to the retaining element such that a proximal end of the swab shaft extends into the cavity, and wherein the piercing member comprises the proximal end of the swab shaft.

16. The device of claim 15, wherein the swab shaft comprises a tube defining a longitudinal passageway therethrough, and wherein, after the liquid chamber seal is pierced, the liquid chamber is in fluid communication with the sensor tube through the passageway.

17. The device of claim 16, wherein the swab shaft defines a radial aperture at its distal end near the swab tip, and wherein, after the liquid chamber seal is pierced, the liquid chamber is in fluid communication with the sensor tube through the passageway and the aperture.

18. The device of claim 1, further comprising a locking mechanism that is operable to prevent the movable element from moving in a proximal direction after the liquid chamber seal is pierced.

19. The device of claim 1, wherein the liquid in the liquid chamber is in an amount of about 500 uL, 1 mL, 1.5 mL, 2 mL, 2.5 mL, 3 mL, 3.5 mL, or 4 mL.

20. A device for detecting an infection in a wound, comprising:
 a) an indicator unit; wherein the indicator unit comprises:
  i. a sensor tube having an open proximal end; and
  ii. a sensor positioned in the sensor tube; and
 b) a swab unit, wherein the swab unit comprises:
  i. a swab shaft having a proximal end and a distal end;
  ii. a swab tip positioned at the distal end of the swab shaft; and
  iii. a swab handle connected to the swab shaft at the proximal end of the swab shaft, the swab handle being configured to sealingly engage the open proximal end of the sensor tube, the swab handle defining a liquid chamber and the swab handle containing a liquid in the liquid chamber to automatically release the liquid into the sensor tube with the swab tip positioned within the sensor tube and the swab handle sealingly engaged to the open proximal end of the sensor tube, and the swab handle comprising a liquid chamber seal positioned at a distal end of the liquid chamber, the indicator unit further comprising a piercing member fixedly attached to the sensor tube at a location whereby the piercing member contacts the liquid chamber seal only when a distal end of the swab handle is inserted into the sensor tube, and inserting the distal end of the swab handle into the sensor tube causing the piercing member to pierce the liquid chamber seal to release the liquid into the sensor tube.

21. The device of claim 20, wherein the piercing member is a piercing ring.

22. A device for detecting an infection in a wound, comprising:
 a) an indicator unit; wherein the indicator unit comprises:
  i. a sensor tube having an open proximal end; and
  ii. a sensor positioned in the sensor tube; and
 b) a swab unit, wherein the swab unit comprises:
  i. a swab shaft having a proximal end and a distal end;
  ii. a swab tip positioned at the distal end of the swab shaft; and
  iii. a swab handle connected to the swab shaft at the proximal end of the swab shaft, the swab handle being configured to sealingly engage the open proximal end of the sensor tube, wherein the swab handle defines a liquid chamber and wherein the swab handle contains a liquid in the liquid chamber and is structured to automatically release the liquid into the sensor tube after the swab tip is positioned within the sensor tube and the swab handle is sealingly engaged to the open proximal end of the sensor tube, and wherein the swab handle comprises a liquid chamber seal positioned at a distal end of the liquid chamber, wherein the indicator unit further comprises a piercing ring attached to the sensor tube at a location whereby the piercing ring contacts the liquid chamber seal only when a distal end of the swap handle is inserted into the sensor tube, and wherein the piercing ring is positioned within the sensor tube such that insertion of the distal end of the swap handle into the sensor tube causes the piercing ring to pierce the liquid chamber seal to release the liquid into the sensor tube.

23. The device of claim 22, wherein a proximal edge of the piercing ring comprises at least one sharp piercing edge that contacts and pierces the liquid chamber seal when the swab unit is inserted into the indicator unit.

24. The device of claim 22, wherein the piercing ring is affixed to an inner wall of the sensor tube.

25. The device of claim 22, wherein the piercing ring comprises a plurality of piercing edges that contact and pierce the liquid chamber seal when the swab unit is inserted into the indicator unit.

* * * * *